United States Patent [19]

Briggs

[11] 4,442,212

[45] Apr. 10, 1984

[54] MONOTHIOGLYCEROL AS THIOL-PROTECTOR IN LYOPHILIZED MATERIALS

[75] Inventor: Anglis R. Briggs, Newark, Del.

[73] Assignee: E. I. Du Pont de Nemours & Company, Wilmington, Del.

[21] Appl. No.: 205,793

[22] Filed: Nov. 10, 1980

[51] Int. Cl.$^3$ .............................................. C12N 9/96
[52] U.S. Cl. ................................ 435/188; 252/174.12
[58] Field of Search ................... 435/188; 252/174.12, 252/DIG. 12; 424/94

[56] References Cited

U.S. PATENT DOCUMENTS 3,066,211 11/1962 Milford et al. ..................... 260/85.5
4,118,279 10/1978 Determann .......................... 435/188
4,247,643 1/1981 Kramer et al. ...................... 435/178

OTHER PUBLICATIONS

G. Szasz, "Proceedings of the Second International Symposium on Clinical Enzymology", 1975, pp. III-1 to 36.

L. G. Morin, Clinical Chemistry, 23 (9) 1569, (1977).

G. Szasz et al., Clinical Chemistry, vol. 24, No. 9, 1557, (1978).

Evans Chemetics, Inc.'s brochure on "Thioglycerol".

A. P. MacKenzie, "The Physico–Chemical Basis for the Freeze–Drying Process", International Sumposium on Freeze–Drying of Biological Products, vol. 36, pp. 51–67, (1977).

Primary Examiner—Hiram H. Bernstein

[57] ABSTRACT

A lyophilized product containing monothioglycerol, sulfhydryl-requiring enzyme and a specially prepared serum matrix, useful in the clinical laboratory when reconstituted, is provided.

8 Claims, No Drawings 4,442,212

MONOTHIOGLYCEROL AS THIOL-PROTECTOR IN LYOPHILIZED MATERIALS

DESCRIPTION

TECHNICAL FIELD

This invention relates to thiol-protector agents used with sulfhydryl-requiring enzymes and more particularly to monothioglycerol as a thiol-protector in lyophilized materials.

BACKGROUND ART

Certain proteins require the presence of sulfhydryl groups in their structure for activity and stability. In the presence of oxidizing agents, however, including atmospheric oxygen, the sulfhydryl groups are oxidized to disulfide linkages with concomitant deleterious changes in the protein's properties. These problems are magnified when the protein is in serum-based material or lyophilized.

Addition of excess thiols has been utilized as a means of protection for the sulfhydryl groups of proteins. A large number of thiols has been evaluated for effectiveness as a protective agent against oxidation (G. Szasz, "Proceedings of the Second International Symposium on Clinical Enzymology", 1975, pages III-1 to 36). Szasz examined twenty-seven thiol compounds with creatine kinase, an unstable enzyme. Both possible dimercapto (1,3 and 1,2-dimercapto) glycerols were tested for their effectiveness but monothioglycerol [1-mercapto (or 1-sulfhydryl)-2,3-propanediol] was not included in the evaluation.

Monothioglycerol (MTG, 1-sulfhydryl-2,3-propanediol) has been found to be effective for this purpose; its half-life in solutions in equilibrium with atmospheric oxygen is sufficiently long for practical purposes. However, it has been stated by L. G. Morin, in Clinical Chemistry, Volume 23, No. 9, 1569 (1977), at page 1574 that "(monothioglycerol) would undoubtedly not lyophilize". For this reason, MTG has not been utilized as a sulfhydryl-protector in lyophilized materials.

A. P. MacKenzie, at the International Symposium on Freeze-Drying of Biological Products, Washington, D.C., October, 1976, Proceedings, page 52, reported the lyophilisis of glycerol-containing biological materials. In absence of residual moisture content determinations, however, the artisan is not guided as to the lyophilizability of glycerol-containing materials. Moreover, even if glycerol-containing materials are lyophilizable, the artisan again is not guided as to the class of lyophilizable low molecular weight liquids.

G. Szasz, et al. [Clinical Chemistry, Volume 24, No. 9, 1557 (1978)] also investigated MTG but observed gelling of the serum proteins, with 50 mM MTG per liter, after six hours storage at 37° C. These investigators then selected N-acetyl cystein as the protecting agent of choice for creatine kinase isoenzymes.

DISCLOSURE OF THE INVENTION

The lyophilized product of this invention consists essentially of:

(A) monothioglycerol, present in the pre-lyophilized solution to an extent of not less than approximately 2 mmoles/liter of solution and in an amount not leading to gelation of the solution;

(B) sulfhydryl-requiring enzyme; and (C) substantially completely delipified animal serum having low residual levels of enzyme activity.

This product can be reconstituted without showing any significant adverse temperature of hydration effect affording a product in which the enzyme activity remains substantially constant for 24 hours at 4° C.

In the improved process for protecting lyophilizable compositions containing sulfhydryl-requiring enzymes, which includes the addition of thiol-protectors, the improvement comprising the addition of monothioglycerol as the thiol-protector.

DESCRIPTION OF THE INVENTION

Certain enzymes are "sulfhydryl-requiring", that is, they need to maintain their —SH groups in their free, unoxidized form. Atmospheric oxygen causes the oxidation of the —SH groups to the disulfide (S—S) linkage, thereby diminishing enzyme stability and catalytic activity. Among "sulfhydryl-requiring" enzymes are yeast alcohol dehydrogenase, glyceraldehyde-3-phosphate dehydrogenase, papain, RNA polymerase, acetate thiokinase, and creatine kinase isoenzymes.

In contrast, some proteins require disulfide linkages for their activity. Such proteins, for example, ribonuclease, IgG, insulin, do not require thiol-protectors during storage and exposure to atmospheric oxygen.

Many thiols have been utilized previously as thiol-protectors for "SH-requiring" enzymes. Among the best of the thiols for this purpose are N-acetyl cystein (NAC), glutathione (GSH), mercaptoethanol, dithiothreitol, dithioerythritol, and monothioglycerol (MTG). Some of these, such as NAC and GSH, have also been incorporated into enzyme solutions and subsequently lyophilized. In the aforementioned review article, comparing some twenty-seven thiols as thiol-protectors, NAC was found to have optimum overall properties. MTG, however, which has many advantages over other thiols, such as being nonionic and having longer half-life than NAC in enzyme solutions, has been said to be unsuitable for incorporation into enzyme solutions which will be lyophilized.

It has now been found unexpectedly that the inclusion of MTG into solutions containing "SH-requiring" enzymes leads to lyophilizable products containing such enzymes and a specially prepared human serum matrix. When reconstituted, such products are stable for periods of time sufficient for use in the clinical laboratory. In the lyophilized form, they appear to be stable indefinitely. 2–100 mmoles/liter of MTG in the pre-lyophilized composition is the useful range of concentration with 20 mmoles/liter being a preferred amount. The upper limit is that amount of MTG which does not cause gelation of the composition.

From accelerated experiments it is predicted that when the "SH-requiring" enzyme is CKMM, then products containing this isoenzyme, MTG, and a specially prepared serum, which is substantially completely delipified and has low residual levels of enzyme activity, would exhibit little or no detectable loss of enzyme activity in the lyophilized form after one year of storage at $4 \pm 2°$ C. For CKMM, the expected range of concentration in the pre-lyophilized composition is 20–40 enzyme units/liter at the low end of the scale up to approximately 3,000 units/liter at the high end.

The finding that MTG can be utilized with enzymes to afford lyophilizable product led to unexpected benefits. To be useful as control products in the clinical analysis field, an enzyme-containing lyophilized product must have two characteristics often very difficult to achieve simultaneously. First, there must be substantially no or only very small temperature of hydration effect and, second, there must only be very slight changes in enzyme activity upon standing after reconstitution (rehydration) of the lyophilized product.

The temperature of hydration effect is the phenomenon of variability of recovered enzyme activity from a lyophilized material upon rehydration caused by the differences in the temperature of water used. For obvious practical purposes, for use in the clinical laboratory, lyophilized products must have a small temperature of hydration effect to permit reproducible analytical results. This temperature of hydration effect is calculated by reconstituting the lyophilized product with water at 20°, 25°, and 30° C., followed by the measurement of enzyme activity of the rehydrated solutions. The slope of the line fitting these data is determined by a least squares calculation to obtain the temperature of hydration effect in enzyme units/°C. The %/°C. value is calculated from the enzyme activity value of 25° C. It is desired that the temperature of hydration effect not exceed ±0.5%/°C. It is further desired that this low temperature of hydration effect be coupled to an enzyme activity change not exceeding ±5% during 24 hours standing at 4° C. (after rehydration of the lyophilized material).

In a comparison study, the thiol-protectors N-acetyl cystein (NAC) and the subject of this invention, monothioglycerol (MTG), were incorporated at various levels into a specially prepared human serum matrix containing creatine kinase MM isoenzyme and various levels of a buffer, 2-amino-2-hydroxymethyl-1,3-propanediol (TRIS).

The specially prepared substantially completely delipified animal (including human) serum having low residual levels of enzyme activity and its preparation have been described in U.S. Pat. No. 4,264,471 issued Apr. 28, 1981 to Briggs and U.S. application Ser. No. 155,220, filed June 2, 1980 to M. D. du Pont. The above are hereby incorporated by reference. This serum comprises the bulk of the pre-lyophilized composition from which the lyophilized product of this invention is prepared.

In the comparison study, the pH of the solutions was adjusted to 7.2 with HCl, the solutions were lyophilized and then rehydrated. Temperature of hydration effect data and those showing the change in CKMM activity upon standing for 24 hr. at 4° C. are shown below:

| | NAC as Thiol Protector | | | |
|---|---|---|---|---|
| Run no. | NAC (mmoles/ liter) | Buffer (TRIS, mmoles/ liter) | Temperature of Hydration Effect[1] (%/°C.) | Change in CKMM Activity[1] (%) |
| 1 | 10 | 100 | 0.11 | −10.5 |
| 2 | 10 | 200 | 1.5 | −7.7 |
| 3 | 10 | 300 | 4.1 | +1.8 |
| 4 | 20 | 100 | 0.25 | −6.5 |
| 5 | 20 | 200 | 1.2 | −6.5 |
| 6 | 20 | 300 | 3.5 | +1.5 |
| 7 | 30 | 100 | 0.11 | 10.9 |
| 8 | 30 | 200 | 0.97 | −4.6 |
| 9 | 30 | 300 | 3.5 | +1.1 |

[1]CKMM activity was measured by using CK test packs with E. I. du Pont de Nemours and Company's aca instrument.

| | MTG as Thiol Protector | | | |
|---|---|---|---|---|
| Run no. | NAC (mmoles/ liter) | Buffer TRIS, mmoles/ liter | Temperature of Hydration Effect[1] (%/°C.) | Change in CKMM Activity[1] (%) |
| 1 | 10 | 100 | 0.59 | +2.8 |
| 2 | 10 | 200 | 2.4 | +4.1 |
| 3 | 10 | 300 | 3.5 | +7.7 |
| 4 | 20 | 100 | 0.22 | +2.1 |
| 5 | 20 | 200 | 1.6 | +3.5 |
| 6 | 20 | 300 | 3.2 | +6.8 |
| 7 | 30 | 100 | 0.56 | +1.1 |
| 8 | 30 | 200 | 1.1 | +1.8 |
| 9 | 30 | 300 | 4.2 | +8.2 |

[1]See footnote above.

As can be seen from the above tables, while NAC does provide either acceptable temperature of hydration effect or within-limits change of enzyme activity, there were no runs which showed acceptable values for both properties simultaneously. On the other hand, the composition of this invention, utilizing MTG as the thiol protector, is acceptable from both standpoints, especially when low levels of buffer are utilized. (Higher levels of buffer presumably lead to higher levels of ion concentration which may cause a higher temperature of hydration effect.)

It was found further that the half-life of the SH-group of NAC in the specially prepared substantially completely delipified human serum described above is approximately 4 hours when measured in a reconstituted TRIS-buffered system (pH=7.2) at 16°–20° C. The comparable SH-group half-life for MTG in the same system is 22.6 hours, further indicating the superiority of this thiol protector. The data from which these half-life values were derived are presented below:

| N—Acetyl Cystein (NAC) (nominal SH-group concentration, prior to lyophilization: 5 mmoles/liter) | |
|---|---|
| elapsed time (hr.) | measured SH-group concentration[1,2] |
| 0 | 2.87 |
| 0.5 | 2.67 ± 0.08 |
| 1 | 2.38 ± 0.20 |
| 2 | 1.92 ± 0.15 |
| 7 | 0.98 ± 0.14 |

[1]SH-concentration is measured by using Ellman's Reagent, 5,5'-dithiobis (2-nitrobenzoic acid)
[2]The calculated constant for the rate of decay is = 0.1710 hr$^{-1}$

| Monothioglycerol (MTG) (nominal SH-group concentration, prior to lyophilization: 20 mmoles/liter) | |
|---|---|
| elapsed time (hr.) | measured SH-group concentration[1,2] |
| 0 | 17.88 ± 2.0 |
| 3.3 | 16.16 ± 0.05 |
| 20 | 10.05 ± 0.07 |

[1]See footnote above
[2]decay = 0.030649 hr$^{-1}$

A further proof of the unexpected lyophilizability of MTG in the compositions of this invention was derived from the analysis of the moisture content of the lyophilized product of this invention. Karl Fisher moisture assays carried out on the lyophilized cake-like material, see Example, indicated an average moisture content of 0.696±0.075% by weight, which value is in the normal range for lyophilized products in general. Coupled with the data presented above (approximately 90% of the SH-groups are still present upon reconstitution after lyophilization, t=0), MTG is shown to be a useful thiol-protector possessing all of the required characteristics and unexpectedly affording lyophilized products of superior properties.

The lyophilized product of this invention can be reconstituted with water to obtain products useful as a calibrator for use in the clinical laboratory. Since the lyophilized product is stable, it can be rehydrated at the appropriate time in the clinical laboratory and used as a control product in conjunction with, for example, automatic clinical analyzers utilized in measuring enzyme activity such as creatine kinase.

EXAMPLE

A. Preparation of Pre-Lyophilized Product

To a 2-liter quantity of human serum prepared according to Example A–D of U.S. Pat. No. 4,264,471 is added 40 mmoles of MTG at room temperature. To this solution is then added a CKMM solution (itself having an MTG concentration of 20 mmoles/liter), to obtain a final enzyme activity of 816 units/liter. A frozen cynomolgus monkey (*Macaca fasicicularis*) heart, weighing 9.5 grams, is cut into pieces, placed in a Waring blender along with 48 mL of buffer containing 15 mmoles/liter tris(hydroxymethyl) aminomethane, 95 mmoles/liter sodium chloride and 20 mmoles/liter monothioglycerol, adjusted to pH 8.1 with hydrochloric acid and blended for 30 seconds. The material is then centrifuged for 30 minutes at 5000 rpm in a Du Pont Sorvall RC-5 centrifuge equipped with an SS-34 rotor followed by filtration through glass wool. A column (5 cm×17.5 cm) of Pharmacia DEAE-Sepharose CL6B is packed and equilibrated using a solution of 15 mmoles/liter tris(hydroxymethyl) aminomethane and 95 mmoles/liter sodium chloride adjusted to pH 8.1 with hydrochloric acid. The supernatant material from the above filtration step is placed on the DEAE-Sepharose column and the column is washed with the same buffer with which it was equilibrated. Fractions of the column eluate are assayed using Du Pont's aca instrument and CK test assay packs. Fractions containing more than 1 M U/L CK activity are pooled. This pool is brought to 20 mmoles/liter in monothioglycerol by addition of monothioglycerol and stored at 4° C. until use.) This solution is then diluted with an equal volume of water. An assay of this final solution shows an enzyme activity of 426 units/liter.

B. Preparation of Lyophilized Product

The diluted solution from (A) above is pumped into amber vials, 6.2 ml/vial, the vials are placed onto the shelves of a lyophilizer, and the temperature of the shelves is lowered to −20° C. The contents of the vials are thus frozen, placed under a 40-80 micron vacuum, and maintained at −20° C. for 12 hours. After this time period the shelf temperature is allowed to rise to +10° C. and the vials are kept at this temperature, still under vacuum, for 24 hours. The contents of the vials are finally dried under vacuum for 2 hours at 25° C., resulting in a dry cake weighing approximately 197 mg. The vials are sealed under a 40-micron vacuum and stored at 4±2° C.

The lyophilized product can be tested by rehydrating the contents of a vial with 3 ml. of deionized water and analyzed for enzyme activity change and temperature of hydration effect.

Two pilot lots prepared as described above show temperature of hydration effect of 0.12%/°C. and 0.21%/°C., respectively, well within the desired limit of 0.5%/°C. and +0.8% and +0.85%, respectively, of activity change upon standing. The average freeze-dried product in a vial contains 2.4 enzyme units of CKMM/3 ml. of reconstituted solution.

I claim:

1. A water reconstitutable lyophilized product of a solution consisting essentially of:
   (A) monothioglycerol, present in the pre-lyophilized solution to an extent of not less than 2 mmoles/liter of solution and in an amount not leading to gelation of the solution;
   (B) sulfhydryl-requiring enzyme; and
   (C) substantially completely delipified animal serum having low residual levels of enzyme activity.

2. The lyophilized product of claim 1 wherein the monothioglycerol is present to an extent wherein the monothioglycerol is present to an extent of 2–100 mmoles/liter of solution.

3. The lyophilized product of claim 1 wherein the monothioglycerol is present at a concentration of 20 mmoles/liter of solution.

4. The lyophilized product of claim 1 wherein the sulfhydryl-requiring enzyme is CKMM.

5. A rehydrated composition of a lyophilized product consisting essentially of an aqueous solution of:
   (A) monothioglycerol, present in the pre-lyophilized solution to an extent of not less than 2 mmoles/liter of solution and in an amount not leading to gelation of the solution;
   (B) sulfhydryl-requiring enzyme; and
   (C) substantially completely delipified animal serum having low residual levels of enzyme activity
wherein the composition shows no significant temperature of hydration effect and whose enzyme activity remains substantially constant for 24 hours at 4° C.

6. The rehydrated composition of claim 5 wherein the temperature of hydration effect is less than ±0.5%/°C. and the enzyme activity changes less than ±5%.

7. In an improved process for protecting water reconstitutable lyophilizable composition containing sulfhydryl-requiring enzymes which includes the step of adding thiol-protectors, wherein the improvement comprises the addition of monothioglycerol as the thiol-protector.

8. The improved process of claim 7 wherein the amount of monothioglycerol in the lyophilizable composition is 2–100 mmoles/liter of the composition.

* * * * *